United States Patent [19]

Kulik et al.

[11] Patent Number: 4,893,634
[45] Date of Patent: Jan. 16, 1990

[54] DEVICE FOR CLEANSING MEASURING PRESSURE IN THE COLON

[75] Inventors: Yaroslav P. Kulik; Alexei A. Malaev, both of Blagoveschensk Amurskoi, U.S.S.R.

[73] Assignee: Problamnaya Nauchno-Issledovatelskaya Laboratoria Vspomogatelnogo Krovoobraschenia, Blagoveschensk, U.S.S.R.

[21] Appl. No.: 77,895

[22] Filed: Jul. 27, 1987

[51] Int. Cl.[4] ............................................. A61B 5/10
[52] U.S. Cl. .................................... 128/748; 604/30; 604/54; 604/118
[58] Field of Search ........................ 128/4-6, 128/748; 604/27, 30-34, 54, 118, 119, 150; 73/756

[56] References Cited

U.S. PATENT DOCUMENTS

| | | | |
|---|---|---|---|
| 2,873,739 | 2/1959 | Whann | 604/118 |
| 3,900,022 | 8/1975 | Widran | 604/118 |
| 3,982,533 | 9/1976 | Wiest | 604/118 |
| 4,423,727 | 1/1984 | Widran et al. | 128/748 |
| 4,637,814 | 1/1987 | Leiboff | 604/27 |
| 4,722,350 | 2/1988 | Armeniades | 128/748 |
| 4,779,611 | 10/1988 | Grooters | 128/4 |

Primary Examiner—Jerome L. Kruter
Attorney, Agent, or Firm—Lilling & Greenspan

[57] ABSTRACT

A device for cleansing the colon includes an elastic housing with an oval-shaped end and provided with an aspiration channel and a discharge channel isolated from each other, each channel having its own outlet port in the end of the housing. An endoscope is built into the aspiration channel and is provided with a transparent balloon on its working portion, while the discharge channel accommodates an open-end capillary tube whose open end is brought outwards through the end of the housing, the other end of the tube being connected to a pressure measurement instrument.

4 Claims, 2 Drawing Sheets

DEVICE FOR CLEANSING MEASURING PRESSURE IN THE COLON

BACKGROUND OF THE INVENTION

FIELD OF THE INVENTION

The invention relates to medical apparatus and is concerned particularly with devices for cleansing the colon.

the invention can find widespread application in clinical practice for emergency preoperative treatment of the colon, in treatment of paresis or paralysis of the intestine, within the post-operative period and the preoperative period in cardiosurgical patients inclined to constipation at the decompensation stage just before the surgery, as well as in patients suffering from paralysis of the pelvic cavity organs.

DESCRIPTION OF THE PRIOR ART

A device for cleansing or evacuation of the colon, i.e., a cleansing or evacuant enema is extensively known in the art.

However, use of such an enema fails to provide adequate cleansing of the colon, since the process proceeds without monitoring the internal conditions of the intestine. In addition, the procedure involves an active patient's tension.

Another prior-art device for cleansing the colon is known to comprise a cylinder-shaped housing with an oval-shaped end, said housing having a discharge and an aspiration channel, both being isolated from each other and having respective outlet ports in the end portion of the housing, a reservoir for a lavation solution, and a receptacle, each of which communicate, through a respective piping, with the discharge and aspiration channels, respectively, a means for regulating the delivery head and the suction head of the discharged and aspirated fluid, respectively (cf. SU, A, No. 806,040).

Application of such a device enables one to regulate the delivery and suction head of the discharged and aspirated fluid, respectively. However, the colon evacuation process with this device, like the one discussed above, operates without monitoring, the amount of the lavation solution injected into the colon is out of control by measuring the intraintestinal pressure. The device is inserted in the colon in a blind way without visual control, the intensity of the flow of the evacuant solution being regulated without allowance for the consistency of the fecal masses. In addition, the known device fails to provide an adequate cleansing of the distal segments of the colon, since the device is of the rigid construction.

SUMMARY OF THE INVENTION

It is an object of the present invention to provide more adequate evacuation of the colonic contents (bulk).

It is another object of the invention to provide an adequate cleansing of both the proximal and the distal colon segments.

It is a further object of the invention to provide a visual control over the internal colonic conditions.

It is additional object of the invention to provide a control over the intraintestinal pressure in the course of the colonic evacuation.

The essence of the invention resides in a device for cleansing the colon, comprising a cylinder-shaped housing with an ovalshaped end, said housing having a discharge channel and an aspiration channel isolated from each other and provided with outlet ports in the end portion of the housing. A reservoir is provided for a lavation solution, and a receptacle, the former communicating, through a piping, with the discharge channel, while the latter communicates, via another piping, with the aspiration channel. Means is used for regulating the delivery head and the suction head of the fluids being discharged and aspirated, respectively. According to the invention, the housing is made of an elastic material, and an endoscope is incorporated in the aspiration channel, whose working portion is brought outwards through the end of the housing, and a transparent inflatable balloon is attached to the endoscope working portion.

It is expedient that, for the purpose of monitoring the intraintestinal pressure, a capillary tube be accommodated in the discharge channel, one of whose ends would be open and brought outwards via an opening in the end portion of the housing, while the other capillary tube end be connected to an instrument for measuring the pressure outside the cylinder-shaped housing.

The device for cleansing the colon, according to the invention, makes it possible to carry out an adequate cleansing or evacuation of both the proximal and the distal colonic segments, since its housing is made from an elastic material and the device is provided with the means for control of the internal conditions of the colon, i.e., an endoscope and a manometer for measuring the intraintestinal pressure. Provision of such control and monitoring means in the device enables one adjust the pressure head of the lavation solution as a function of the parameters of the internal intestinal conditions, which contributes to more safety of the colonic evacuation procedure, cuts down the operating time and makes the evacuation more adequate, especially with respect to the distal colonic segments.

BRIEF DESCRIPTION OF THE DRAWINGS

In what follows the present invention is exemplified by the disclosure of specific embodiments thereof to be had in conjunction with the accompanying drawings, wherein.

DESCRIPTION OF THE PREFERRED EMBODIMENT

Figure 1:
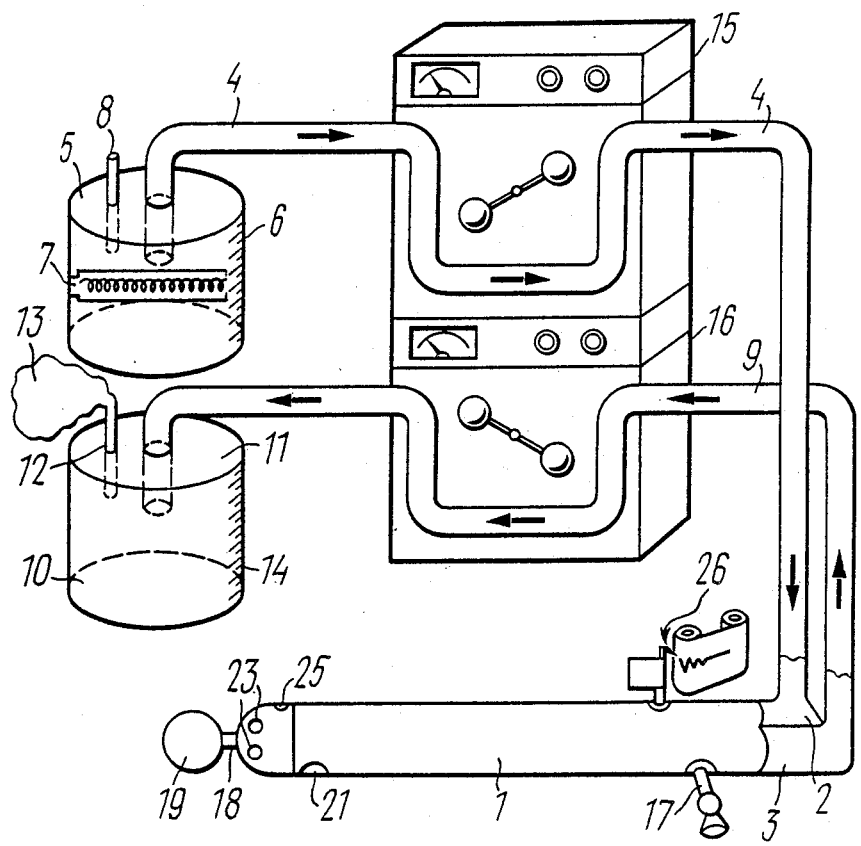
FIG. 1 is a general schematic view of a device for cleansing the colon.
Figure 2:
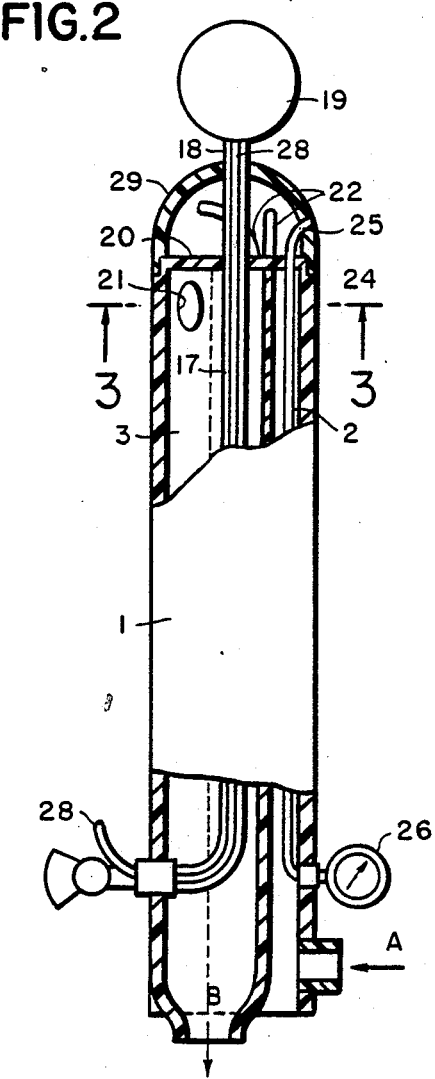
FIG. 2 is a front elevational, partly sectional view of a cylinder-shaped housing.
Figure 3:
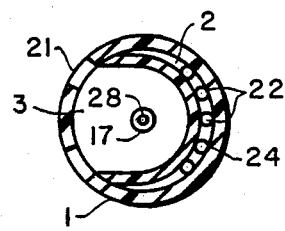
FIG. 3 is a section taken along the line III—III in FIG. 2.

The device for cleansing the colon as illustrated in FIG. 1, comprises a cylinder-shaped housing 1 made from an elastic material, such as silicone and having an oval-shaped working end made of, e.g., protacryle. The housing 1 has a discharge channel 2 and an aspiration channel 3, both channels being isolated from each other. The discharge channel 2 communicates, through a piping 4, with a reservoir 5 for lavation solution provided with scale 6 to read the fluid level in the reservoir off said scale, and equipped also with an electric heater 7 and a thermometer 8. The aspiration channel 3 communicates, through a piping 9, with a receptacle 10 provided with a hermetically tight cover 11, into which a tube 12 carrying an inflatable rubber bulb 13 is built, and with a scale 14 to indicate the fluid level in the receptacle 10. A variable-capacity pump 15 is provided in the piping 4, and a variable-capacity pump 16 is incorporated in the piping 9. An endoscope 17 is provided in the aspiration channel 3 (FIGS. 2, 3), a working portion 18 of said endoscope being brought outwards, using a hermetic sealing, through an opening in the oval end of the housing 1, and carrying a transparent inflatable or expandable balloon 19 provided with an air conduit 29 for admitting excessive pressure to the balloon 19.

Figure 4:
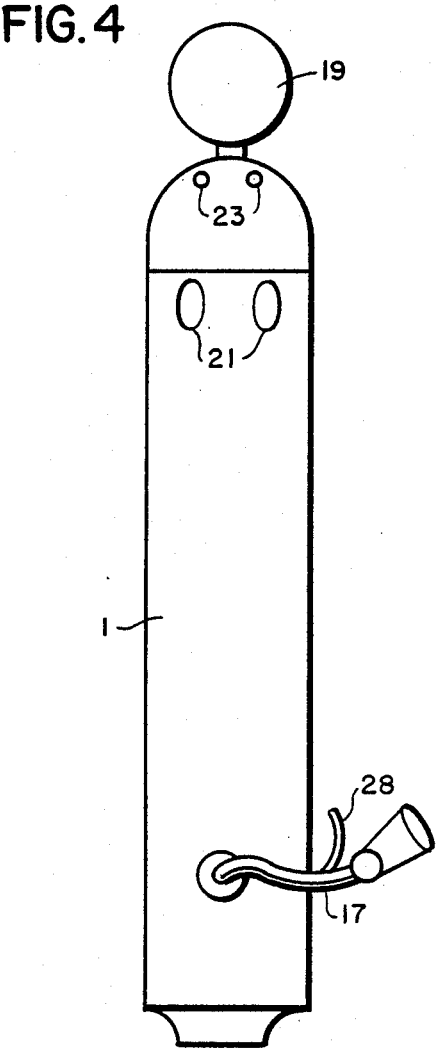
FIG. 4 is a right-side elevation of FIG. 2.

An internal partition 20 is provided in the end portion of the housing 1, while ports 21 (FIGS 2, 3, 4) are made in the aspiration channel 3 nearby the partition 20, adapted to receive the colonic contents (bulk), and there are provided openings in the discharge channel 2 and in the partition 20, into which outlet connectors 22 are fitted (four in number in this particular embodiment), adapted to feed the lavation solution from the channel 2 to the colon through ports 23 (FIG. 4) in the end of the housing 1, said ports 23 being spread uniformly over the end surface of the housing 1. The aspiration channel 3 (FIG. 3) has a round-shaped cross-section, while the discharge channel is slit-shaped in cross-section, the ratio of the cross-sectional areas of the channels 2 and 3 equalling 3:1.

In a preferred embodiment of the present invention the discharge channel 2 accommodates a capillary tube 24, one of its ends being open and brought outwards through an opening 25 in the end of the housing 1, while the other end of the capillary tube is connected to a pressure measurement instrument 26, e.g., an electronic manograph.

The device for cleansing the colon operates as follows.

The elastic housing 1 is introduced into the rectum, a pressure is applied to the transparent balloon 19 which, upon having been inflated, prevents penetration of the fecal matter onto the working portion of the endoscope 17, thus enabling one to examine visually the non-prepared colon as well as the movement of the housing 1 therein, and providing safe manipulations under visual control. Then the lavation solution is delivered, by the variable-capacity pump 15, from the reservoir 5 along the piping 4 to the discharge channel 2 and further on through the outlet connections 22 and the ports 23 into the colon. The intensity (flow rate) of the flow of the lavation solution is adjusted within 100 and 2000 ml per minute depending on the consistency of the fecal matter. It is due to small diameter of the discharge ports 23 that a powerful wash-out effect is provided. The preset temperature of the lavation solution is maintained by the electric heater 7 and monitored by the thermometer 8, while the rate of the lavation solution flow is read off the scale 6.

The rate of flow of the aspirated fluid withdrawn from the colon through the ports 21 into the channel 3 and further on along the piping 9 into the receptacle 10, is adjusted by the pump 16 depending on the intraintestinal pressure value, which is measured by the electric manograph connected to the capillary tube 24, which extends into the opening 25 in the housing 1. The pump 16 provides for pulsating rarefaction in the colon, thus preventing the end of the housing 1 from being sucked to the colonic walls. The washed out feces and the gases are delivered along the piping 9 to the receptacle 10 hermetically closed by the cover 11 provided with the tube 12 onto which the rubber bulb 13 is fitted, which gets inflated by the gases delivered from the colon. The amount of the laving water and the feces is indicated on the scale 14. Simultaneously with the colonic evacuation the colonic mucosa is assessed endoscopically. A total amount of the solution spent for evacuation of the colon is 9 to 14 liters, the procedure taking 10 to 20 minutes to carry out. Upon termination of the procedure the elastic housing 1 of the device is disconnected from the pipings 4 and 9 and from the monitoring instruments and is sent for sterilization.

What is claimed is:

1. A device for cleansing the colon, comprising:
a cylinder-shaped housing made of an elastic material;
working end of said housing;
a discharge channel in said housing;
ports of said discharge channel in said housing end adapted for delivering a lavation solution into the colon;
an aspiration channel in said housing, isolated from said discharge channel;
ports of said aspiration channel in said housing end adapted for receiving the contents of said colon washed out by said lavation solution;
a reservoir for said lavation solution;
a first piping communicating said reservoir for the lavation solution with said discharge channel;
a receptacle for accepting the contents of said color washed out by said lavation solution;
a second piping which establishes communication between said receptacle and said aspiration channel;
an endoscope accommodated in said aspiration channel and having a working portion brought outwards from said channel through an opening in said housing working end;
an expandable transparent balloon provided on said working portion of said endoscope extending through and out of said aspiration channel through an opening in said working end of said housing;
means for expanding said balloon after it has been introduced into the colon to achieve effective pressurization and sealing in the area of contact between the walls of the balloon and the colon walls;
a tube means extending in said discharge channel for transmitting the pressure in the colon, one end of said tube means extending out of said working end of said housing and the other end of said tube means extending out of a proximal end of said housing for connection to a pressure measuring means; and
means for adjusting the pressure head and the suction head in said respective first and second pipings.

2. A device for cleansing the colon as defined in claim 1, wherein said tube means is a capillary tube.

3. A device for cleansing the colon as defined in claim 1, further comprising a pressure measurement instrument connected to said other end of said tube.

4. A device for cleansing the colon as defined in claim 3, wherein said working end of said housing is oval-shaped.

* * * * *